United States Patent [19]

Bueding et al.

[11] 4,234,583
[45] Nov. 18, 1980

[54] 2-CHLORO-4-(4-LOWER ALKYL-1-PIPERAZINYL)BENZENEME-THANOL, N$^\omega$-OXIDES AND METHODS FOR THEIR PREPARATION

[75] Inventors: Ernest Bueding, Baltimore, Md.; Leslie M. Werbel; Donald F. Worth, both of Ann Arbor, Mich.

[73] Assignee: Edna McConnell Clark Foundation, New York, N.Y.

[21] Appl. No.: 965,371

[22] Filed: Nov. 30, 1978

[51] Int. Cl.$^3$ .................. A61K 31/495; C07D 295/00
[52] U.S. Cl. ..................................... 424/250; 544/383
[58] Field of Search ........................ 544/383; 424/250

[56] References Cited

U.S. PATENT DOCUMENTS

| | | | |
|---|---|---|---|
| 2,578,053 | 12/1951 | Denton et al. | 544/383 |
| 2,724,712 | 11/1955 | Goldman et al. | 544/383 |
| 3,714,167 | 1/1973 | Archer et al. | 544/386 |

*Primary Examiner*—Jose Tovar
*Attorney, Agent, or Firm*—Sprung, Felfe, Horn, Lynch & Kramer

[57] ABSTRACT

2-Chloro-4-(4-lower alkyl-1-piperazinyl)benzenemethanol, N$^\omega$-oxides and their acid addition salts. These compounds are prepared by oxidizing the corresponding 2-chloro-4-(4-lower alkyl-1-piperazinyl)benzenemethanol. In addition, pharmaceutical compositions comprising said N-oxides and methods for treating schistosomiasis are disclosed.

5 Claims, No Drawings

2-CHLORO-4-(4-LOWER ALKYL-1-PIPERAZINYL)BENZENEMETHANOL, N$^\omega$-OXIDES AND METHODS FOR THEIR PREPARATION

SUMMARY AND DETAILED DESCRIPTION

The present invention relates to new organic piperazine-N-oxides useful in the treatment of schistosomiasis. More particularly, the invention relates to compounds of the formula

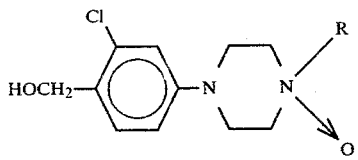

and acid addition salts thereof wherein R is methyl, ethyl, propyl or isopropyl; preferably where R is methyl.

In accordance with the invention, the compounds of formula I and acid addition salts thereof, are prepared by oxidizing a compound of the formula

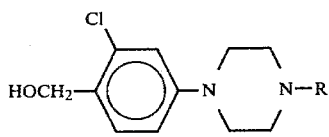

wherein R is as previously defined for formula I, and adjusting the pH to give the N-oxide or a salt thereof, as desired. The oxidation is generally carried out employing a peroxy acid, such as 3-chloroperbenzoic acid, perbenzoic acid, peracetic acid, etc. or hydrogen peroxide. Generally, about equimolar amounts of oxidizing agent and substrate are employed.

The reaction is carried out at from about $-20°$ C. to about 40° C. for from about a couple of minutes to about 24 hours, preferably about 0° C. to 25° C. for about one hour.

Advantageously, the oxidation is effected in an inert solvent such as hydrocarbons, chlorinated hydrocarbons, alkanols, aliphatic ketones, water, etc.

The starting materials of the formula II are prepared according to the procedures described in U.S. Pat. No. 3,714,167.

The term acid addition salt is intended to mean salts formed by the addition of an acid, such as hydrochloric acid, sulfuric acid, benzoic acid, acetic acid, etc. The preferred salts are relatively non-toxic salts which are generally termed pharmaceutically acceptable salts.

The compounds of this invention may exist in anhydrous form as well as solvated, including hydrated, forms. In general, the solvated forms are equivalent to the anhydrous or unsolvated form for the purposes of this invention.

The compounds of this invention have the specific advantage over the corresponding des-N-oxide compounds in that the compounds are non-mutagenic in a test designed to determine mutagenicity which is described in *J. Pharm. Exp. Therap.*, 200, 1 (1977).

In addition, the compounds of the invention are significantly less toxic when administered via the intramuscular route than the corresponding des-N-oxide.

In accordance with the invention, oral pharmaceutical compositions are produced by formulating a compound of the invention, optionally with other active ingredients, in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg., preferably 5 to 100 mg., of the active ingredient per dosage unit so that the entire amount to be administered during a day can be made up from a reasonable number of dosage units.

The compounds of the invention may be administered parenterally, especially intramuscularly, in a suitable vehicle, such as isotonic saline solution, which may contain other active ingredients, buffering agents, preservatives, etc.

The aforementioned compounds are administered in dosage unit form, with the dose adjusted to the needs and tolerances of the individual patient. The usual mammalian dosage range for a 70 kg. subject is from 10 to 1000 mg. per day (0.1 mg. to 14 mg. per kg. of weight per day), preferably 50 to 250 mg. per day (0.7 mg to 3.6 mg. per kg. of weight per day), optionally in divided portions.

Preparation of the novel compounds is shown in the following illustrative examples:

EXAMPLE 1

A solution of 5.0 g of 3-chloroperoxybenzoic acid in 50 ml of chloroform is added slowly with stirring to a solution of 5.0 g of 2-chloro-4-(4-methyl-1-piperazinyl)-benzenemethanol in 50 ml of chloroform. After stirring 0.5 hr the solution is extracted with 5% potassium carbonate. The aqueous extracts are then placed on a column of Amberlite XAD-2 resin. The column is washed with water, and then with methanol. Concentration of the methanol eluate gives a clear, colorless oil. Upon standing, crystallization occurs, yielding 3.0 g of the desired 2-chloro-4-(4-methyl-1-piperazinyl)benzenemethanol, N$^\omega$-oxide, mp 224°–226° C. (decomposition).

The hydrochloride salt may be prepared as follows: A solution of 0.43 g of hydrogen chloride in 2 ml of 2-propanol is added dropwise with stirring to 3.0 g of 2-chloro-4-(4-methyl-1-piperazinyl)benzenemethanol, N$^\omega$-oxide dissolved in 25 ml of 2-propanol. Upon dilution with ether and cooling the desired 2-chloro-4-(4-methyl-1-piperazinyl)benzenemethanol, N$^\omega$-oxide, monohydrochloride precipitates.

EXAMPLE 2

A solution of 1.36 g of 3-chloroperoxybenzoic acid in 15 ml of chloroform is added dropwise with stirring to a solution of 2.0 g of 2-chloro-4-(4-ethyl-1-piperazinyl)-benzenemethanol in 35 ml of chloroform. After stirring 1 hr at room temperature, an additional 0.43 g of 3-chloroperoxybenzoic acid is added. The solution is then extracted with aqueous sodium carbonate. The aqueous layers are placed in a column of Amberlite XAD-2 resin. The column is washed with water and then methanol. Concentration of the methanol eluate yields the desired 2-chloro-4-(4-ethyl-1-piperazinyl)benzenemethanol, N$^\omega$-oxide. Crystallization from ether gives 0.82 g of the hemihydrate, mp 183°–185° C. (decomposition).

EXAMPLE 3

A solution of 3.1 g of 3-chloroperoxybenzoic acid in 30 ml of chloroform is added dropwise at 0° C. to a solution of 4.04 g of 2-chloro-4-[4-(1-methylethyl)-1-piperazinyl]benzenemethanol in 90 ml of chloroform. After stirring 0.5 hr the solution is washed with 20 ml of saturated aqueous potassium carbonate. The chloroform layer is then dried over solid potassium carbonate and concentrated to dryness. Recrystallization from 2-propanol gives 0.7 g of 2-chloro-4-[4-(1-methylethyl)-1-piperazinyl]-benzenemethanol, N$^\omega$-oxide, mp 167° C. (decomposition), as colorless crystals.

Alternatively, purification can be achieved through chromatography. A methanol solution of 3 g of crude 2-chloro-4-[4-(1-methylethyl)-1-piperazinyl]benzenemethanol, N$^\omega$-oxide is placed in a column of 300 g of silica gel and eluted with methanol. The appropriate fractions are combined on the basis of thin layer chromatography, and concentrated to dryness. There is obtained 2 g of 2-chloro-4-[4-(1-methylethyl)-1-piperazinyl]benzenemethanol, N$^\omega$-oxide, essentially identical with that obtained above.

The compounds of the invention are useful in the treatment of schistosomiasis. Compounds of this invention, when placed in the primary screen in mice described in *Am. J. Trop. Med. Hyg.*, 21, 302 (1972) yielded the following data which is reported in Table I:

TABLE 1

Effects of Single Oral Doses (Aqueous Solutions) of 2-Chloro-4-(4-alkyl-1-piperazinyl)benzenemethanol, N$^\omega$-oxides Against Mature *S. mansoni* Infections in Mice

| R | Schistosome Strain | Dose mg/kg | % Reduction Live Worms | % Mice Cured | No. of Tests |
|---|---|---|---|---|---|
| CH$_3$ | Puerto Rican/Michigan | 300 | 99 | 87 | 1 |
| CH$_3$ | Puerto Rican/Michigan | 75 | 90 | 52 | 5 |
| CH$_3$ | Puerto Rican/Michigan | 40 | 79 | 43 | 11 |
| CH$_3$ | Puerto Rican/Sterling Winthrop | 75 | 69 | 60 | 5 |
| CH$_3$ | Puerto Rican/Sterling Winthrop | 40 | 56 | 33 | 3 |
| CH$_3$ | Puerto Rican/Walter Reed | 100 | 100 | 100 | 2 |
| CH$_3$ | St. Lucian | 150 | 16 | 0 | 2 |
| CH$_3$ | Brazilian | 40 | 88 | 51 | 3 |
| CH$_3$ | Brazilian | 20 | 73 | 0 | 1 |
| CH$_3$ | Liberian | 50 | 25 | 0 | 2 |
| C$_2$H$_5$ | Puerto Rican/Michigan | 75 | 92 | 71 | 1 |
| CH(CH$_3$)$_2$ | Puerto Rican/Michigan | 125 | 90 | 57 | 1 |
| CH(CH$_3$)$_2$ | Puerto Rican/Michigan | 75 | 100 | 100 | 1 |
| CH(CH$_3$)$_2$ | Puerto Rican/Michigan | 40 | 57 | 19 | 5 |
| CH(CH$_3$)$_2$ | Puerto Rican/Sterling Winthrop | 75 | 25 | 0 | 1 |
| CH(CH$_3$)$_2$ | Puerto Rican/Walter Reed | 75 | 85 | 72 | 1 |
| CH(CH$_3$)$_2$ | Puerto Rican/Walter Reed | 40 | 96 | 75 | 1 |
| CH(CH$_3$)$_2$ | St. Lucian | 75 | 75 | 57 | 1 |
| CH(CH$_3$)$_2$ | St. Lucian | 40 | 50 | 0 | 1 |
| CH(CH$_3$)$_2$ | Brazilian | 40 | 32 | 0 | 1 |
| CH(CH$_3$)$_2$ | Liberian | 125 | 100 | 100 | 1 |
| CH(CH$_3$)$_2$ | Liberian | 75 | 42 | 0 | 2 |

The preferred compound of the invention, when placed in a secondary test in monkeys described in *Am. J. Trop. Med. Hyg.* 15, 705 (1966) gave the following data:

TABLE II

Effects of 2-chloro-4-(4-methyl-1-piperazinyl)benzenemethanol, N^ω-oxide Against Mature *S. mansoni* (Puerto Rican/Walter Reed Strain) Infections in Monkeys (*Cebus apella*)

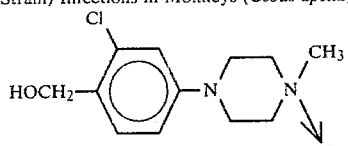

| Dose mg/kg | % Reduction Live Worms | Final Egg Count |
|---|---|---|
| 50 × 4 | 92 | 0 |
| 50 × 4 | 91 | 0 |

The absence of mutagenic activity is shown in the trials reported in the following table:

TABLE III

Mutagenic Activity Using *Salmonella typhimurium* (TA-98 and TA-100)

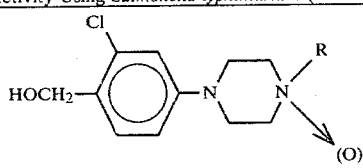

| | | Revertants per n mole | | | | | | | | |
|---|---|---|---|---|---|---|---|---|---|---|
| | | In Vitro | | | | Mouse Urine | | | | Host Mediated |
| | | TA-98 | | TA-100 | | TA-98 | | TA-100 | | |
| R | N-oxide | −S$_9$ | +S$_9$ | −S$_9$ | +S$_9$ | −S$_9$ | +S$_9$ | −S$_9$ | +S$_9$ | TA-98  TA-100 |
| CH$_3$ | Yes | — | — | — | — | — | — | — | — | —    — |
| CH$_3$ | No | — | — | — | 0.1 | | | | | |
| CH(CH$_3$)$_2$ | Yes | — | — | — | 0.007 | | | | | |

"—" indicates result not significantly different than control

In addition, the compounds of the invention are significantly less toxic when administered via the intramuscular route than the corresponding des-N-oxide.

The reduced toxicities of the N-oxides are shown in the following table:

TABLE IV

Approximate Acute Intramuscular LD$_{50}$ Values in Uninfected Mice

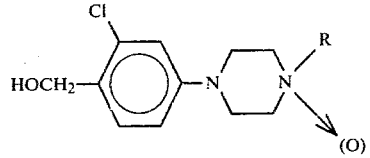

| R | N-oxide | des N-oxide |
|---|---|---|
| CH$_3$ | 1500 | 200 |
| C$_2$H$_5$ | >250 | 150 |
| CH(CH$_3$)$_2$ | >1500 | 100 |

It will be appreciated that the instant specification and examples are set forth by way of illustration and not limitation, and that various modifications and changes may be made without departing from the spirit and scope of the present invention.

We claim:

1. A compound of the formula

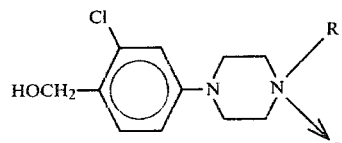

and acid addition salts thereof wherein R is methyl, ethyl, propyl, or isopropyl.

2. A compound according to claim 1 wherein R is methyl.

3. A pharmaceutical composition comprising an anti-schictosomiasis effective amount of compound according to claim 1 and a pharmaceutical vehicle.

4. A composition according to claim 3 in the form of a unit dose.

5. A method for treating schistosomiasis which comprises administering to a patient afflicted therewith an anti-schistosomiasis effective amount of a compound according to claim 1.

* * * * *